United States Patent [19]

Burke

[11] Patent Number: 6,087,533
[45] Date of Patent: Jul. 11, 2000

[54] RHODIUM CATALYZED CARBONYLATION OF AN ALLYLIC BUTENOL OR BUTENYL ESTER TO BETA-GAMMA UNSATURATED ANHYDRIDES

[75] Inventor: Patrick Michael Burke, Wilmington, Del.

[73] Assignees: E I. du Pont de Nemours and Company, Wilmington, Del.; DSM Desotech Inc., Geleen, Netherlands

[21] Appl. No.: 09/215,410

[22] Filed: Dec. 18, 1998

[51] Int. Cl.[7] ............................. C07C 51/54; C07C 51/56
[52] U.S. Cl. .............................................. 562/890; 562/891
[58] Field of Search ...................................... 562/890, 891

[56] References Cited

U.S. PATENT DOCUMENTS

| | | | |
|---|---|---|---|
| 3,852,346 | 12/1974 | Forster et al. . | |
| 4,140,865 | 2/1979 | Fernholz et al. | 562/319 |
| 4,563,309 | 1/1986 | Wegman | 260/549 |
| 4,603,020 | 7/1986 | Kojima et al. | 260/549 |
| 4,625,058 | 11/1986 | Fujiwa et al. | 562/519 |
| 4,642,370 | 2/1987 | Alper et al. | 560/100 |
| 4,781,868 | 11/1988 | Langerbeins . | |
| 5,334,755 | 8/1994 | Yoneda et al. | 562/519 |

FOREIGN PATENT DOCUMENTS

| | | | |
|---|---|---|---|
| 0 273 489 | 11/1987 | European Pat. Off. | C07C 67/38 |
| 0 338 730 A1 | 4/1989 | European Pat. Off. | C07C 57/03 |
| 0 428 979 A2 | 11/1990 | European Pat. Off. | C07C 57/03 |
| 36363 | 9/1972 | Japan . | |
| 47005 | 11/1972 | Japan . | |

*Primary Examiner*—Gary Geist
*Assistant Examiner*—Robert W. Deemie

[57] ABSTRACT

A process for the carbonylation of allylic butenol or butenyl ester of a carboxylic acid (e.g., crotyl acetate, 3-acetoxybutene-1 and mixtures thereof) in an anhydrous carboxylic acid solvent and production of beta-gamma unsaturated carboxylic acid anhydride (e.g., 3-pentenoic acid anhydride) utilizing a rhodium-containing catalyst (e.g., dicarbonylacetylacetonate rhodium(I)) promoted with a metal iodide (e.g., dicarbonylacetylacetonate rhodium(I), or the like). The following representative reaction showing a crotyl ester (i.e., a carboxylic acid ester of 2-buten-1-ol) as the reactant producing a corresponding pentenoic acid anhydride is illustrative of the overall carbonylation.

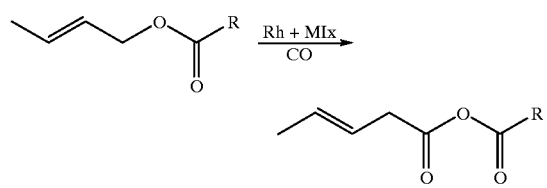

Suitable allylic compounds are of the form

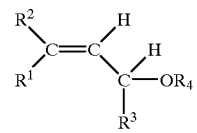

where one of the groups $R^1$, $R^2$, and $R^3$ is methyl and the other two groups are H and wherein $R_4$ is selected from the group consisting of H and

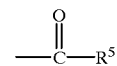

wherein $R^5$ is selected from the group consisting of a $C_1$ to $C_{10}$ alkyl. Such a process is particularly useful in the production of beta-gamma unsaturated carboxylic acid anhydride without promoting the back reaction producing butadiene and a carboxylic acid.

4 Claims, No Drawings

RHODIUM CATALYZED CARBONYLATION OF AN ALLYLIC BUTENOL OR BUTENYL ESTER TO BETA-GAMMA UNSATURATED ANHYDRIDES

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to a process involving the catalytic carbonylation of an allylic butenol or a butenyl ester of a carboxylic acid in a carboxylic acid solvent to produce a beta-gamma unsaturated carboxylic acid anhydride. More specifically but not by way of limitation, the invention relates to the use of a rhodium-containing catalyst promoted by a metal iodide salt under anhydrous conditions for the carbonylation of crotyl acetate, 3-acetoxybutene-1 and mixtures thereof to produce 3-pentenoic acid anhydride.

2. Description of Related Art

The use of rhodium-containing catalyst with various types of co-catalysts and promoters for the carbonylation of a variety of saturated and unsaturated organic compounds is generally known. For example, U.S. Pat. No. 4,603,020 claims a process for the carbonylation of O-acetyl compounds, such as acetic anhydride, at 130 to 250° C. using a rhodium catalyst and an aluminum accelerator. U.S. Pat. No. 4,625,058 teaches a similar process but uses boron, bismuth or tertiary amide compounds as accelerators. U.S. Pat. No. 4,642,370 discloses a process for the carbonylation of hydrocarbyl halides which uses a boron, silicon, aluminum, or zirconium accelerator. U.S. Pat. No. 4,563,309 claims a process for the production of carboxylic acid anhydride of the formula $RC(O)O(O)CCH_3$ by reaction of a methyl carboxylate ester of formula $RC(O)OCH_3$ with carbon monoxide in the presence of a rhodium catalyst and a phosphorous-containing ligand.

European patent application 0 428 979 A2 discloses the carbonylation of allylic butenols and butenol esters using a rhodium catalysts and a hydrogen bromide or hydrogen iodide promoter under anhydrous conditions for the production of 3-pentenoic acid. However, the use of the hydrogen iodide promoter results in a back reaction producing butadiene and a carboxylic acid. The present invention alleviates this problem and as such is viewed as an improvement relative to this disclosure.

BRIEF SUMMARY OF THE INVENTION

In view of the above, it has now been discovered that the anhydrous carbonylation of crotyl esters to acid anhydrides can be readily achieved with high selectivity and high activity by use of a rhodium-containing catalyst provided a metal iodide or a metal salt which can be converted to an iodide under reaction condition, e.g., a metal acetate with HI, is employed to promote the reaction. It is felt that the metal iodide in an anhydrous carboxylic acid solvent serves mechanistically as a buffered source of iodide which in turn minimizes the undesirable back reaction of the crotyl ester to butadiene and carboxylic acid.

Thus the present invention provides a process for the carbonylation of allylic butenol or butenyl ester of a carboxylic acid and production of beta-gamma unsaturated carboxylic acid anhydride comprising the steps of: (a) reacting an allylic butenyl ester of a carboxylic acid with carbon monoxide in the presence of a rhodium-containing catalyst and a metal iodide promoter in a $C_1$ to $C_{20}$ carboxylic acid under anhydrous conditions; and (b) recovering a beta-gamma unsaturated carboxylic acid anhydride. In one particular embodiment of the invention the allylic butenyl ester of a carboxylic acid is selected from the group consisting of crotyl acetate, 3-acetoxybutene-1 and mixtures thereof and the beta-gamma unsaturated carboxylic acid anhydride is 3-pentenoic acid anhydride. In another embodiment the metal iodide promoter is selected from the group consisting of as $CoI_2$, $BI_3$, $AlI_3$, $GaI_3$, $GeI_3$, $SnI_4$, $LaI_3$, $TiI_4$, $ZrI_4$, $CrI_3$, $MnI_3$, $NiI_2$, $ZnI_2$, and $HgI_2$. Preferably, the metal iodide promoter is cobalt iodide.

DETAILED DESCRIPTION OF INVENTION

The process of the present invention involves a rhodium catalyzed carbonylation of an allylic compound to produce a beta-gamma unsaturated carboxylic acid anhydride wherein the rhodium-containing catalyst is promoted by the use of a metal iodide salt and the carbonylation reaction is performed under anhydrous conditions. The allylic compound being carbonylated is an allylic butenyl ester of a carboxylic acid or the equivalent such as an allylic butenol dissolved in a carboxylic acid. The following representative reaction showing a crotyl ester (i.e., a carboxylic acid ester of 2-buten-1-ol) as the reactant producing a corresponding pentenoic acid anhydride is illustrative of the overall carbonylation.

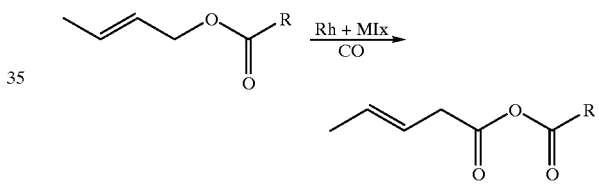

Suitable allylic compounds are of the form

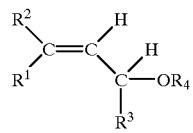

where one of the groups $R^1$, $R^2$, and $R^3$ is methyl and the other two groups are H and wherein $R_4$ is selected from the group consisting of H and

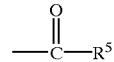

wherein $R^5$ is selected from the group consisting of a $C_1$ to $C_{10}$ alkyl. It should be appreciated that acceptable allylic compounds includes both cis and trans isomers, other positional isomers such as that illustrated by 3-alkoybutene-1 and crotyl ester as well as mixtures of various allylic compounds. Also, for purposes of the present invention, when the allylic compound is a butenyl alcohol (i.e., when R4 is H) the presence of the carboxylic acid solvent leads to in-situ ester formation and thus total equivalency relative to the above illustrative carbonylation reaction.

The reaction can be performed at a temperature in the range of 40° C. to about 200° C. Below 40° C. the reaction becomes too slow to be commercially feasible, and above 200° C. the formation of undesirable products leads to significant yield losses. Preferably the reaction temperature is between 90° C. and 150° C. and most preferably between 90° C. and 150° C.

Suitable total pressures for the reaction are in the range 25 to 3,000 psig. Preferably the pressure is between 100 and 2,000 psig with 200 to 1,000 psig being most preferred.

The source of the carbon monoxide (CO) reactant for the present invention is not crucial. Commercially available grades of carbon monoxide are acceptable. As such, the carbon monoxide can contain inert impurities such as carbon dioxide, methane, nitrogen, noble gasses, and other hydrocarbon having up to four carbon atoms. Preferably the carbon monoxide also contains hydrogen typically at about a ten mole percent concentration relative to the carbon monoxide. At least 1 molar equivalent of carbon monoxide to allylic butenyl ester is needed. Typically, an excess of CO is used.

Suitable solvents for this process are anhydrous carboxylic acids of up to twenty carbon atoms. Such solvents include aliphatic and aromatic carboxylic acid solvents and mixtures thereof. The most preferred solvents are the $C_2$ to $C_{10}$ aliphatic monocarboxylic acids and most preferably the solvent is anhydrous acetic acid or 3-pentenoic acid.

The rhodium catalyst can be provided from any source or by any material which will produce rhodium ions under the carbonylation reaction conditions. Among the materials which can be employed as the source of the rhodium catalyst are rhodium metal, rhodium salts, rhodium oxides, rhodium carbonyl compounds, organorhodium compounds, coordination compounds of rhodium, and mixtures thereof. Specific examples of such compounds include, but are not limited to, $RhCl_3$, $RI_3$, $Rh(CO)_2I_3$, $Rh(CO)I_3$, $Rh_4(CO)_{12}$, $Rh_6(CO)_{16}$, $Rh(acac)_3$, $Rh(CO)_2(acac)$, $Rh(C_2H_4)_2(acac)$, $[Rh(C_2H_4)_2Cl]_2$, $[Rh(CO)_2Cl]_2$, $[Rh(CO)_2Br]_2$, $Rh(COD)(acac)$, $[Rh(COD)Cl]_2$, $RhCl(CO)(PPh_3)_2$, $Rh_2[O_2C(CR_2)_6CH_3]_4$, and $Rh_2(acetate)_4$, where acac is acetylacetonate, COD is 1,5-cyclooctadiene, and Ph is phenyl. Rhodium compounds containing bidentate phosphorus or nitrogen ligands should be avoided. Preferred sources of rhodium catalyst include rhodium(I) compounds such as $[Rh(CO)_2Cl]_2$, $[Rh(COD)Cl]_2$, $Rh(COD)(acac)$, and rhodium iodide compounds such as $RhI_3$ and $Rh(CO)_2I_3$.

Suitable concentrations of rhodium in the reaction are in the range of 0.005 to 0.50% by weight of rhodium metal based on the reaction medium. Preferably the concentration of rhodium is in the range of 0.02 to 0.20 wt %. Although high reaction rates on a per Rh basis can be obtained even at low concentrations of Rh, it is generally more economical to operate at Rh concentrations above 0.01 wt %. Similarly, Rh concentrations below 2.0 wt % are preferred to minimize the formation of unwanted by-products.

The rhodium, which may be pre-formed or generated in situ, must be promoted by a metal iodide under anhydrous reaction conditions, to achieve a satisfactory rate and selectivity to pentenoic acid anhydrides. Examples of suitable promoters are iodides of Groups IIB, IIIA, IIIB, IVA, IVB, VIB, VII, VIII of the periodic table. Preferred promoters are $CoI_2$ $BI_3$, $AlI_3$, $GaI_3$, $GeI_3$, $SnI_4$, $LaI_3$, $TiI_4$, $ZrI4$, $CrI_3$, $MnI3$, $NiI_2$, $ZnI_2$, and $HgI_2$. Most preferred promoter is cobalt iodide.

The molar ratio of promoter to rhodium can be in the range of about 1:1 to about 30:1. Although high selectivities to the desired 3-pentenoic acid anhydride can be obtained even at low promoter to rhodium ratios, the rate of formation of 3-pentenoic acid anhydride on a per Rh basis decreases significantly when the molar ratio of promoter to rhodium is less than 1. This decrease in reaction rates, coupled with the high cost of rhodium makes it more economical to use promoter to rhodium ratios greater than 1:1. Similarly, the molar ratio of promoter to rhodium must be less than about 30 to obtain reasonable yields of the unsaturated acid anhydride. Preferably, the molar ratio of promoter to rhodium is between about 2:1 and about 6:1.

Reaction times can be varied and depend on choice of reactants, solvent, catalyst and promoter as well as their respective concentration and reaction conditions such as temperature and pressure. Residence times of the order of about 1 minute to about 20 hours are acceptable.

The reaction of the present invention may be carried out in a batch or continuous mode. The products can be isolated and recovered by any of the techniques generally known in the art including by example but not limited thereto, extraction, distillation or the like.

The following examples are present to further illustrate specific features and advantages of the present invention and as such are not intended to limit the scope of the invention. The conversion data reported is based on quantitative measurement of the relative amount of reactant that is not consumed by chemical reaction (i.e., all isomers). The selectivity to the desired 3-pentenoic acid anhydride is based on and reported as the amount of methyl ester after esterification of the reaction product and as such includes free 3-pentenoic acid inherently produced by anhydride exchange with the carboxylic acid solvent or the like. The comparative examples (Table 2) show that selectivity to methyl-3-pentenoate (M3P) is very low when alkyl iodides are used in place of the metal iodide promoter. When lithium iodide is used, the rate of the reaction is very low.

EXAMPLE 1

Carbonylation of 3-Acetoxybutene-1 using a Rhodium Catalyst and a Cobalt Iodide Promoter:

A 25 mL glass lined pressure vessel was charges with 5 mL of a solution containing 9.1 grams (80 mmol) of 3-acetoxybutene-1 (3ACB1), 0.258 grams (1.0 mmol) of dicarbonylacetylacetonate rhodium(I), 0.46 grams (1.47 mmol) of cobalt iodide (i.e., $CoI_2$), and 1.00 grams of o-dichlorobenzene (internal gas chromatograph standard) in 100 mL of acetic acid. The pressure vessel was freed from air by purging first with nitrogen (twice) and then with carbon monoxide containing 10 mol % hydrogen (twice). The vessel was then pressurized to 500 psig of 90/10 $CO/H_2$ and heated to 120° C. with agitation for 3 hours. The heat was shut off, the pressure vessel was allowed to cool to room temperature and the excess gases were vented. The product was analyzed by gas chromatography to determine unreacted butenyl acetates and butadiene. Pentenoic anhydride and pentenoic acid were determined by esterifying a sample of the solution with excess methanol in the presence of p-toluenesulfonic acid to convert anhydrides and pentenoic acid to their methyl esters. The esterified product was analyzed for methyl esters by gas chromatography (GC) on a 30 M J&W Scientific BD-5 capillary GC column. The results of the analysis follow:

| Before esterification | mmol/100 mL | |
|---|---|---|
| Butadiene | 1.1 | |
| 3-Acetoxybutene-1 | 9.5 | |
| Crotyl Acetate (cis & trans isomers) | 2.1 | |
| Conversion = 64.5% | | |
| After Esterification | mmol/100 mL | selectivity |
| Methyl-3-pentenoate | 60.9 | 94.4 |
| Methyl-2-pentenoate | 3.2 | 5.0 |

EXAMPLES 2–14

In a manner analogous to the procedure employed in Example 1, an additional thirteen runs were performed using in each example a different metal iodide promoter. The resulting data for each of these examples as well as the corresponding data from Example 1 are presented in the following Table 1.

TABLE 1

| Example | Metal Iodide | Conversion | Selectivity to M3P |
|---|---|---|---|
| 1 | $CoI_2$ | 64.5 | 94.4 |
| 2 | $BI_3$ | 74.7 | 61.8 |
| 3 | $AlI_3$ | 74.6 | 74.8 |
| 4 | $GaI$ | 71.3 | 85.4 |
| 5 | $GeI_3$ | 75.1 | 87.5 |
| 6 | $SnI_4$ | 73.2 | 72.9 |
| 7 | $LaI_3$ | 41.6 | 87.2 |
| 8 | $TiI_4$ | 74.6 | 83.4 |
| 9 | $ZrI_4$ | 75.0 | 89.0 |
| 10 | $CrI_3$ | 74.0 | 91.7 |
| 11 | $MnI_3$ | 56.7 | 93.5 |
| 12 | $NiI_2$ | 12.8 | 29.8 |
| 13 | $ZnI_2$ | 13.2 | 71.6 |
| 14 | $HgI_2$ | 12.8 | 35.6 |

COMPARATIVE EXAMPLES 1–4

For comparison the procedure utilizes in Example 1 was repeated except that the metal iodide was replaced with HI, an alkyl iodide (2-iodobutane or 1-iodobutane), or lithium iodide. The results are summarized in Table 2.

TABLE 2

| Comparative Example | Additive | Conversion | Selectivity to M3P |
|---|---|---|---|
| 1 | HI | 63.2 | 7.4 |
| 2 | 2-iodobutane | 63.8 | 1.0 |
| 3 | 1-iodobutane | 64.3 | 3.2 |
| 4 | lithium iodide | 2.3 | 47.7 |
| 5 | 1-iodobutane and lithium iodide | 16.9 | 88.2 |

EXAMPLES 15–18

In a manner analogous to the procedure employed in Example 1, an additional four runs were performed except the 3-acetoxybutene-1 was replaced with crotyl acetate and the promoter was a mixture of HI and a metal acetate or chloride salt. The ratio of HI to Rh was 3 and the ratio of metal to Rh was 1. The resulting data are presented in the following Table 3.

TABLE 3

| Example | Metal Promoter | Iodide | Conversion | Selectivity to M3P |
|---|---|---|---|---|
| 15 | $Al(OAc)_2OH$[a] | 57% aq HI | 95.0 | 69.0 |
| 16 | Aluminum Chloride | anh HI/HOAc[b] | 90.1 | 79.8 |
| 17 | Samarium Acetate | anh HI/HOAc | 75.6 | 83.2 |
| 18 | Cobalt Acetate | anh HI/HOAc | 78.4 | 83.0 |

(a) monobasic aluminum acetate (b) a solution of 57% aqueous HI in acetic acid with an amount of acetic acid anhydride equivalent to the water in the aqueous HI The process of the present invention is useful for the preparation of carboxylic acid anhydrides and derivative thereof and in particular the production of 3-pentenoic acid. Such products are useful as difunctional monomers and as intermediates in the synthesis of adipic acid.

Having thus described and exemplified the invention with a certain degree of particularity, it should be appreciated that the following claims are not to be so limited but are to be afforded a scope commensurate with the wording of each element of the claim and equivalents thereof.

I claim:

1. A process for the carbonylation of allylic butenol or a butenyl ester of a carboxylic acid and production of beta-gamma unsaturated carboxylic acid anhydride comprising the steps of:

(a) reacting an allylic butenol or butenyl ester of a carboxylic acid with carbon monoxide in the presence of a rhodium-containing catalyst and a metal iodide promoter selected from the group consisting of iodides of Groups IIB, IIIA, IIIB, IVA, IVB, VIB, VIIB, and VIII of the periodic table in a $C_1$ to $C_{20}$ carboxylic acid solvent under anhydrous conditions; and (b) recovering a beta-gamma unsaturated carboxylic acid anhydride.

2. The process of claim 1 wherein said allylic butenyl ester of a carboxylic acid is selected from the group consisting of crotyl acetate, 3-acetoxybutene-1 and mixtures thereof and said beta-gamma unsaturated carboxylic acid anhydride is 3-pentenoic acid anhydride.

3. The process of claim 2 wherein said metal iodide promoter is selected from the group consisting of $CoI_2$, $BI_3$, $AlI_3$, $GaI_3$, $GeI_3$, $SnI_4$, $LaI_3$, $TiI_4$, $ZrI_4$, $CrI_3$, $MnI_3$, $NiI_2$, $ZnI_2$, and $HgI_2$.

4. The process of claim 3 wherein said metal iodide promoter is cobalt iodide.

* * * * *